US012426911B2

(12) United States Patent
Downey et al.

(10) Patent No.: US 12,426,911 B2
(45) Date of Patent: *Sep. 30, 2025

(54) ADAPTER AND METHODS FOR COUPLING A SURGICAL HANDPIECE TO A CONTROL CONSOLE

(71) Applicant: Stryker Corporation, Kalamazoo, MI (US)

(72) Inventors: Adam D. Downey, Kalamazoo, MI (US); Jason J. Wroblewski, Portage, MI (US)

(73) Assignee: Stryker Corporation, Portage, MI (US)

( * ) Notice: Subject to any disclaimer, the term of this patent is extended or adjusted under 35 U.S.C. 154(b) by 110 days.

This patent is subject to a terminal disclaimer.

(21) Appl. No.: 18/389,881

(22) Filed: Dec. 20, 2023

(65) Prior Publication Data

US 2024/0115288 A1 Apr. 11, 2024

Related U.S. Application Data

(63) Continuation of application No. 16/863,372, filed on Apr. 30, 2020, now Pat. No. 11,871,953.
(Continued)

(51) Int. Cl.
*A61B 17/32* (2006.01)
*A61B 17/00* (2006.01)
*A61B 90/98* (2016.01)

(52) U.S. Cl.
CPC ...... *A61B 17/320068* (2013.01); *A61B 90/98* (2016.02); *A61B 2017/00199* (2013.01);
(Continued)

(58) Field of Classification Search
CPC ........... A61B 2017/00017; A61B 2017/00199; A61B 2017/00225; A61B 2017/00402;
(Continued)

(56) References Cited

U.S. PATENT DOCUMENTS 6,266,551 B1 7/2001 Osadchy et al.
6,850,788 B2 2/2005 Al-Ali
(Continued)

OTHER PUBLICATIONS

International Patent Application No. PCT/IB2020/050314, filed on Jan. 15, 2020.
Non-Provisional U.S. Appl. No. 17/145,223, filed Jan. 8, 2021.

*Primary Examiner* — Mohamed G Gabr
(74) *Attorney, Agent, or Firm* — Howard & Howard Attorneys PLLC

(57) ABSTRACT

An adapter configured to receive a drive signal from a control console and to provide the drive signal to an ultrasonic surgical handpiece. The adapter includes a receptacle for receiving the ultrasonic surgical handpiece and providing the drive signal to the ultrasonic surgical handpiece. The adapter includes a module for detecting a presence of the ultrasonic surgical handpiece and a connector to be inserted into a receptacle of the control console to receive the drive signal from the control console. The adapter includes a radio-frequency identification device coupled to the connector and to a memory storing a maximum and minimum frequency for driving the ultrasonic surgical handpiece. The radio-frequency identification device transmits the maximum and minimum frequency from the memory to the control console via the connector using an RFID protocol in response to the module detecting the presence of the ultrasonic surgical handpiece.

18 Claims, 14 Drawing Sheets

Related U.S. Application Data

(60) Provisional application No. 62/840,786, filed on Apr. 30, 2019.

(52) U.S. Cl.
CPC ............... *A61B 2017/00402* (2013.01); *A61B 2017/00486* (2013.01); *A61B 2017/32007* (2017.08); *A61B 2017/320084* (2013.01)

(58) Field of Classification Search
CPC ........... A61B 2017/00482; A61B 2017/00486; A61B 2017/32007; A61B 2017/320084; A61B 17/320068; A61B 90/98
See application file for complete search history.

(56) References Cited

U.S. PATENT DOCUMENTS

| | | |
|---|---|---|
| 7,273,483 B2 | 9/2007 | Wiener et al. |
| 7,844,314 B2 | 11/2010 | Al-Ali |
| 7,844,315 B2 | 11/2010 | Al-Ali |
| 7,860,553 B2 | 12/2010 | Govari et al. |
| 8,364,224 B2 | 1/2013 | Boyce et al. |
| 8,866,592 B2 | 10/2014 | Brumer et al. |
| 8,983,566 B2 | 3/2015 | Boyce et al. |
| 8,986,302 B2 | 3/2015 | Aldridge et al. |
| 8,994,553 B2 | 3/2015 | Brumer et al. |
| 9,072,474 B2 | 7/2015 | Al-Ali et al. |
| 9,113,831 B2 | 8/2015 | Al-Ali |
| 9,138,180 B1 | 9/2015 | Coverston et al. |
| 9,247,996 B1 | 2/2016 | Merana et al. |
| 9,300,356 B2 | 3/2016 | Winward et al. |
| 9,411,995 B2 | 8/2016 | Brumer et al. |
| 9,439,651 B2 | 9/2016 | Smith et al. |
| 9,527,208 B2 | 12/2016 | Merana et al. |
| 9,578,773 B1 | 2/2017 | Walton et al. |
| 9,619,618 B2 | 4/2017 | Ingmanson |
| 9,693,718 B2 | 7/2017 | Boyce et al. |
| 9,876,320 B2 | 1/2018 | Coverston et al. |
| 10,016,209 B2 | 7/2018 | Downey et al. |
| 10,061,948 B2 | 8/2018 | Jensen et al. |
| 10,219,706 B2 | 3/2019 | Al-Ali |
| 10,298,403 B2 | 5/2019 | Klammer et al. |
| 10,449,570 B2 | 10/2019 | Downey et al. |
| 10,531,835 B2 | 1/2020 | Al-Ali et al. |
| 10,575,892 B2 | 3/2020 | Danziger et al. |
| 10,639,059 B2 | 5/2020 | Groene et al. |
| 10,869,602 B2 | 12/2020 | Al-Ali |
| 11,068,852 B2 | 7/2021 | Dumbauld et al. |
| 11,083,442 B2 | 8/2021 | Walton et al. |
| 2003/0173408 A1 | 9/2003 | Mosher et al. |
| 2006/0129140 A1* | 6/2006 | Todd ....................... A61B 90/98 606/1 |
| 2008/0030343 A1* | 2/2008 | Raybuck ................. A61B 90/90 340/572.7 |
| 2008/0221591 A1 | 9/2008 | Farritor et al. |
| 2011/0208206 A1* | 8/2011 | Diamant ............ A61B 17/2202 606/128 |
| 2012/0316474 A1 | 12/2012 | Bonutti et al. |
| 2014/0066944 A1 | 3/2014 | Taylor et al. |
| 2017/0000552 A1 | 1/2017 | Asher et al. |
| 2017/0071621 A1 | 3/2017 | Downey et al. |
| 2017/0143369 A1 | 5/2017 | Downey et al. |
| 2018/0056328 A1 | 3/2018 | Downey et al. |
| 2019/0201041 A1 | 7/2019 | Kimball et al. |
| 2019/0201137 A1 | 7/2019 | Shelton, IV et al. |
| 2020/0222009 A1 | 7/2020 | Al-Ali et al. |
| 2020/0237398 A1 | 7/2020 | Groene et al. |
| 2020/0345388 A1 | 11/2020 | Downey et al. |
| 2021/0251538 A1 | 8/2021 | Muhsin et al. |
| 2021/0275204 A1 | 9/2021 | Gladstone |

* cited by examiner

ADAPTER AND METHODS FOR COUPLING A SURGICAL HANDPIECE TO A CONTROL CONSOLE

RELATED APPLICATION

The present application is a continuation of U.S. patent application Ser. No. 16/863,372, filed on Apr. 30, 2020, which claims priority to and all the benefits of U.S. Provisional Patent Application No. 62/840,786, filed on Apr. 30, 2019, the entire disclosures of which are each hereby incorporated by reference.

BACKGROUND

Ultrasonic surgical systems are useful for performing certain medical and surgical procedures. Ultrasonic surgical systems may include multiple components, such as an ultrasonic surgical handpiece and a control console. Typically, each control console is configured to provide a drive signal to a certain type of ultrasonic surgical handpiece. This results in a need for many different consoles, and many different end effectors. As such, there remains a need to eliminate the number of different devices in the operating room.

SUMMARY OF THE DISCLOSURE

An adapter configured to receive a drive signal from a control console and to provide the drive signal to an ultrasonic surgical handpiece is provided. The adapter includes a receptacle configured to receive the ultrasonic surgical handpiece and provide the drive signal to the ultrasonic surgical handpiece. The adapter also includes a connector configured to be inserted into a receptacle of the control console, wherein the connector is configured to receive the drive signal from the control console when the connector is coupled to the control console. Additionally, the adapter includes a radio-frequency identification emulator coupled to the connector, wherein the radio-frequency identification emulator is coupled to a memory storing a maximum and minimum frequency for driving the ultrasonic surgical handpiece, the radio-frequency identification emulator being configured to transmit the maximum and minimum frequency from the memory to the control console via the connector using an RFID protocol.

A method of operating a system for providing a drive signal to an ultrasonic surgical handpiece is provided. The system includes the ultrasonic surgical handpiece, a control console, and an adapter. The method includes steps of coupling the adapter to the control console via a connector and coupling the adapter to the ultrasonic surgical handpiece. The method also includes a step of detecting, by a module of the adapter, a presence of the ultrasonic surgical handpiece. Additionally, the method includes a step of transmitting, by a radio-frequency identification emulator of the adapter, a maximum and minimum frequency for driving the ultrasonic surgical handpiece to the control console via the connector using an RFID protocol in response to the module detecting the presence of the ultrasonic surgical handpiece. The method also includes steps of generating, by the control console, the drive signal based on the maximum and minimum frequency for driving the ultrasonic surgical handpiece and receiving, by the adapter, the drive signal from the control console via the connector. Furthermore, the method includes a step of providing, by the adapter, the drive signal to the ultrasonic surgical handpiece.

BRIEF DESCRIPTION OF THE DRAWINGS

Referring now to the drawings, exemplary illustrations are shown in detail. Although the drawings represent examples, the drawings are not necessarily to scale and certain features may be exaggerated or schematic in form to better illustrate and explain a particular aspect of an illustrative example. Any one or more of these aspects can be used alone or in combination with one another. Further, the exemplary illustrations described herein are not intended to be exhaustive or otherwise limiting or restricting to the precise form and configuration shown in the drawings and disclosed in the following detailed description. Exemplary illustrations are described in detail by referring to the drawings as follows.

DETAILED DESCRIPTION

Figure 1A:
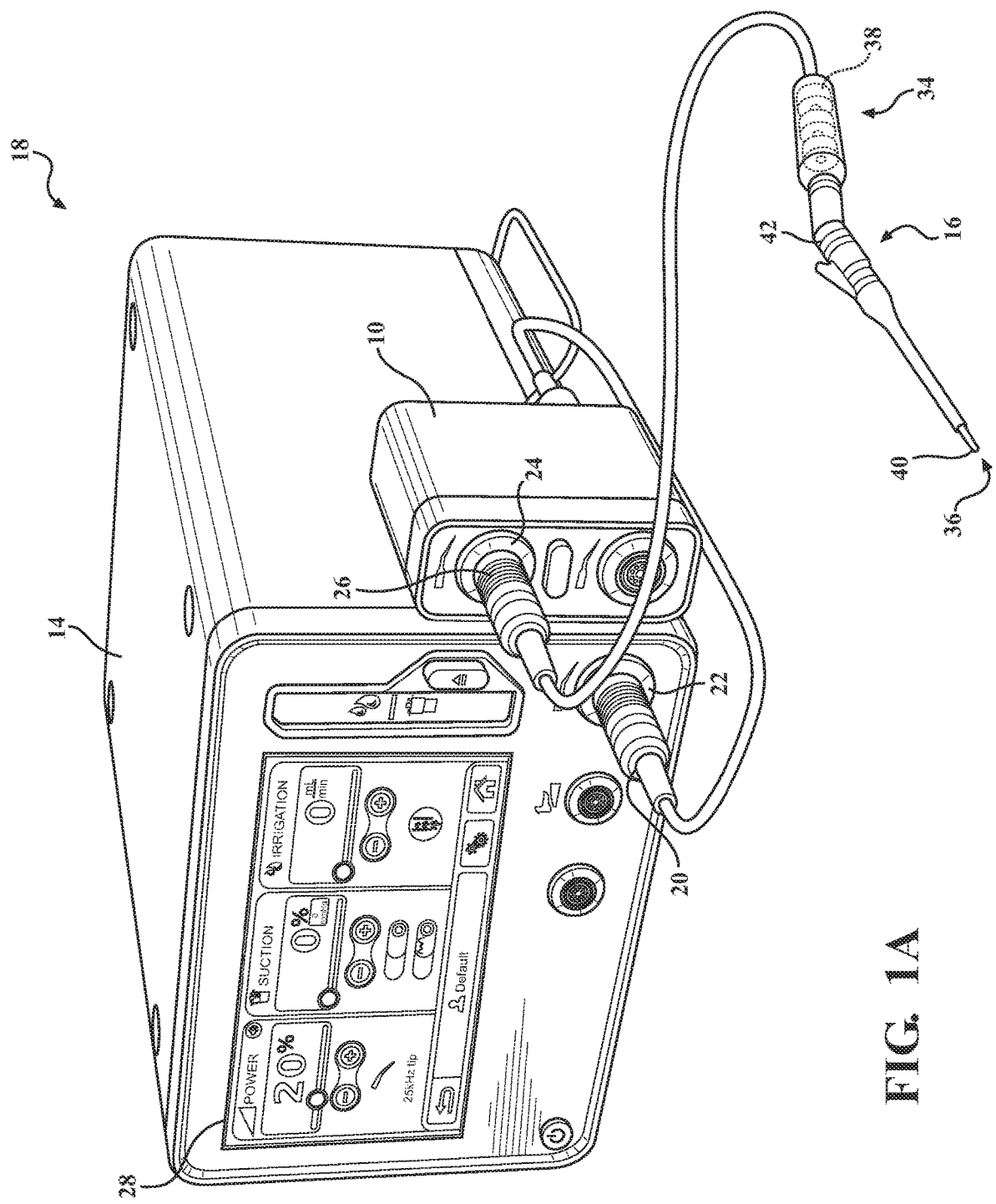
FIG. 1A is a perspective view of an ultrasonic surgical system for providing a drive signal to an ultrasonic surgical handpiece from a control console via an adapter.

Referring to FIG. 1A, an adapter 10 is shown. The adapter 10 is configured to receive a drive signal 12 (shown in FIG. 1B) from a control console 14 and is also configured to provide the drive signal 12 to an ultrasonic surgical handpiece 16. As shown in FIG. 1A, an ultrasonic surgical system 18 for providing the drive signal 12 to the ultrasonic surgical handpiece 16 includes the adapter 10, the control console 14, and the ultrasonic surgical handpiece 16.

The adapter 10 includes a connector 20 configured to be coupled to the control console 14. In the instance of FIG. 1A, the connector 20 is inserted into a receptacle 22 of the control console 14. As such, the adapter 10 is configured to receive the drive signal from the control console 14 via the connector 20 when the connector 20 is coupled to the control console 14.

The adapter 10 also includes a receptacle 24 configured to be coupled to the ultrasonic surgical handpiece 16. For example, in the instance of FIG. 1A, the receptacle 24 receives a connector 26 of the ultrasonic surgical handpiece 16. As such, the adapter 10 is configured to provide the drive signal 12 to the ultrasonic surgical handpiece 16 via the receptacle 24.

Figure 6:
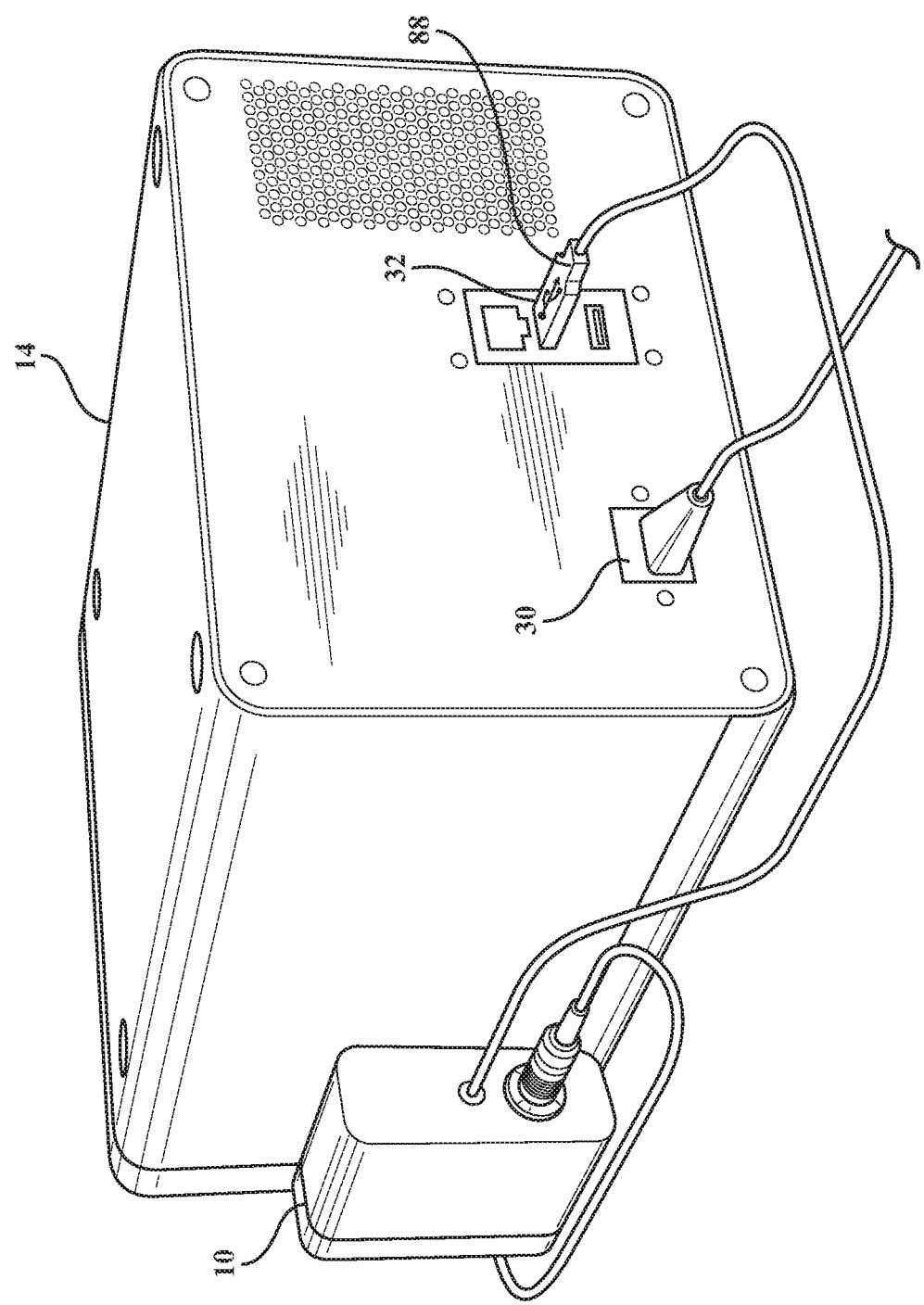
FIG. 6 is a rear perspective view of the adapter and the control console.

The control console 14 may be any suitable control console 14 for generating an alternating current (AC) drive signal as the drive signal 12 for driving the ultrasonic surgical handpiece 16. For example, in the instance of FIG. 1A, the control console 14 includes the receptacle 22, such that the adapter 10 receives the drive signal 12 from the control console 14 via the connector 20 when the connector 20 is coupled to the receptacle 22. Additionally, the control console 14 may include a display 28 configured to display information related to the control console 14, the adapter 10, and/or the ultrasonic surgical handpiece 16. Referring to FIG. 6, the control console 14 may also include a power supply receptacle 30 configured to couple to a power supply (not shown), and a USB port 32 configured to receive a USB connector 88.

Certain components and characteristics of the control console 14 are further described in U.S. Pat. No. 10,016,209 B2, entitled "System and Method for Driving an Ultrasonic Handpiece as a Function of the Mechanical Impedance of the Handpiece," the disclosure of which is hereby incorporated by reference in its entirety. The control console 14 may also be further described in U.S. Pat. No. 10,449,570 B2, entitled "System and Method for Driving an Ultrasonic Handpiece with a Linear Amplifier," the disclosure of which is hereby incorporated by reference in its entirety.

The ultrasonic surgical handpiece 16 may be any suitable surgical handpiece that may be driven by an AC drive signal. For example, in the instance of FIG. 1A, the ultrasonic surgical handpiece 16 includes a proximal end 34 and a distal end 36. ("Proximal" is understood to mean towards the practitioner holding the handpiece, away from the site to which the handpiece is applied. "Distal" is understood to mean away from the practitioner, towards the site to which the handpiece is applied.) The ultrasonic surgical handpiece 16 may also include one or more vibrating piezoelectric drivers 38 (three shown), which are formed from material that, when a current (such as a current from the drive signal 12) is applied to the drivers 38, undergoes a momentary expansion or contraction. Furthermore, the ultrasonic surgical handpiece 16 includes a tip 40, which may be used in a variety of soft-tissue or bone modifying applications. The ultrasonic surgical handpiece 16 may also include a sleeve 42, which may provide suction and/or irrigation at a location adjacent to the tip 40. Additionally, the ultrasonic surgical handpiece 16 may include a memory (not shown), which includes data describing the characteristics of the ultrasonic surgical handpiece 16. The data describing characteristics of the ultrasonic surgical handpiece 16 may include data that identifies the ultrasonic surgical handpiece 16 and/or data that describes characteristics of the drive signal 12 that can be applied to the ultrasonic surgical handpiece 16.

Components and characteristics of one exemplary ultrasonic surgical handpiece 16 are further described, and referred to as "the handpiece", in U.S. Pat. No. 10,016,209 B2, U.S. Pat. No. 10,449,570 B2, and PCT International Application No. PCT/IB2020/050314, which are hereby incorporated by reference in their entirety. The ultrasonic surgical handpiece 16 may be an ultrasonic shear device, an ultrasonic aspirator, or an ultrasonic tissue sealer.

The drive signal 12 generated by the control console 14 may be a variety of AC drive signals suitable for driving the ultrasonic surgical handpiece 16. After the drive signal 12 is received by the ultrasonic surgical handpiece 16, the drive signal 12 is applied to the drivers 38. The application of the drive signal 12 causes the drivers 38 to simultaneously and cyclically expand and contract. Consequently, the tip 40 begins to vibrate for use in soft-tissue or bone modifying applications.

Additionally, the control console 14 may modify the drive signal 12 based on the ultrasonic surgical handpiece 16. For example, each ultrasonic surgical handpiece 16 may include preferences for efficient operation, such as a maximum voltage, a maximum current, and/or a maximum frequency for driving the ultrasonic surgical handpiece 16. The control console 14 provides the drive signal 12 based on a capacitance of the drivers 38, a maximum current of the drive signal 12, a maximum voltage of the drive signal 12, and/or a maximum and minimum frequency of the drive signal 12, all of which may be stored in the memory of the surgical handpiece 16.

In a further instance, the control console 14 may provide the drive signal 12 at a certain frequency to ensure efficient operation of the ultrasonic surgical handpiece 16. For example, one means of ensuring the ultrasonic surgical handpiece 16 operates efficiently is for the control console 14 to provide the drive signal 12 at a resonant frequency of the ultrasonic surgical handpiece 16. When the drive signal 12 is provided at the resonant frequency and at a given voltage, the drive signal 12 induces vibrations in the tip 40 at a relatively large amplitude in comparison to the vibrations induced by a drive signal 12 with the same voltage, but at a frequency that is off-resonance. As described, the resonant frequency of the ultrasonic surgical handpiece 16 may be a function of mechanical components of the ultrasonic surgical handpiece 16, such as the piezoelectric drivers 38, the tip 40, and other mechanical components described in U.S. Pat. No. 10,016,209 B2. Therefore, after the control console 14 determines the resonant frequency based on the mechanical components, the control console 14 continually provides the drive signal 12 at the resonant frequency despite changes to the mechanical components.

The control console 14, using a frequency regulating algorithm, continually provides the drive signal 12 to the ultrasonic surgical handpiece 16 at the resonance frequency despite changes to the mechanical components of the ultrasonic surgical handpiece 16. The frequency regulating algorithm allows the control console 14 to provide the drive signal 12 at a desired frequency and at a desired voltage by controlling a set frequency and a set voltage in a control loop. For instance, if the control console 14 detects a change in an impedance of the piezoelectric drivers 38 or the tip 40, the control console 14 may modify a magnitude of the set voltage or the set frequency to account for the change in the mechanical components. As such, by modifying the set voltage and the set frequency, the control console 14 continues to provide the drive signal 12 at the resonant frequency. This reduces the need for surgical personnel to have to continuously adjust the drive signal 12 to ensure that the tip 40 continuously vibrates at the resonant frequency.

The adapter 10 allows the control console 14 to provide the drive signal 12 to a variety of different types of ultrasonic surgical handpieces 16 using the frequency regulating algorithm. As described, the frequency regulating algorithm advantageously reduces the need for surgical personnel to have to continuously adjust the drive signal 12. The adapter 10 allows this advantage to be realized for ultrasonic surgical handpieces 16 that are not configured to couple to the control console 14 and/or ultrasonic surgical handpieces 16 to which the control console 14 is not configured to provide the drive signal 12. For example, the adapter 10 may allow the control console 14 to provide the drive signal 12 to ultrasonic surgical handpieces 16 from a manufacturer not supported by the control console 14 and/or to a future or legacy ultrasonic surgical handpiece 16.

Figure 1B:
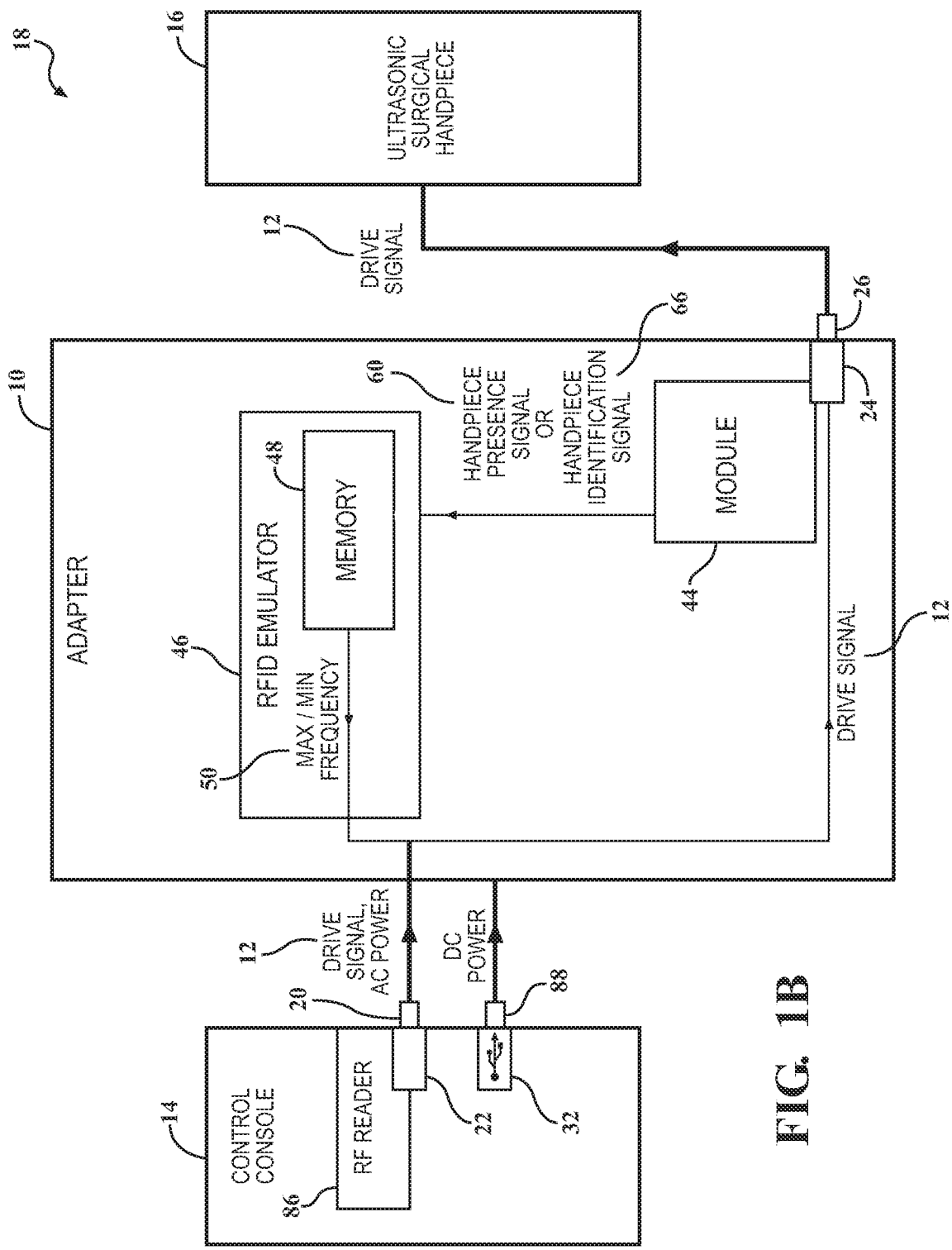
FIG. 1B is a schematic view of the ultrasonic surgical system.

The adapter 10 is further shown in FIG. 1B. As shown, the adapter 10 includes a module 44, which is configured to detect a presence of the ultrasonic surgical handpiece 16 when the ultrasonic surgical handpiece 16 is coupled to the control console 14. The module 44 configured to detect the presence of the ultrasonic surgical handpiece 16 may be optionally included or omitted from the adapter 10.

Figure 2:
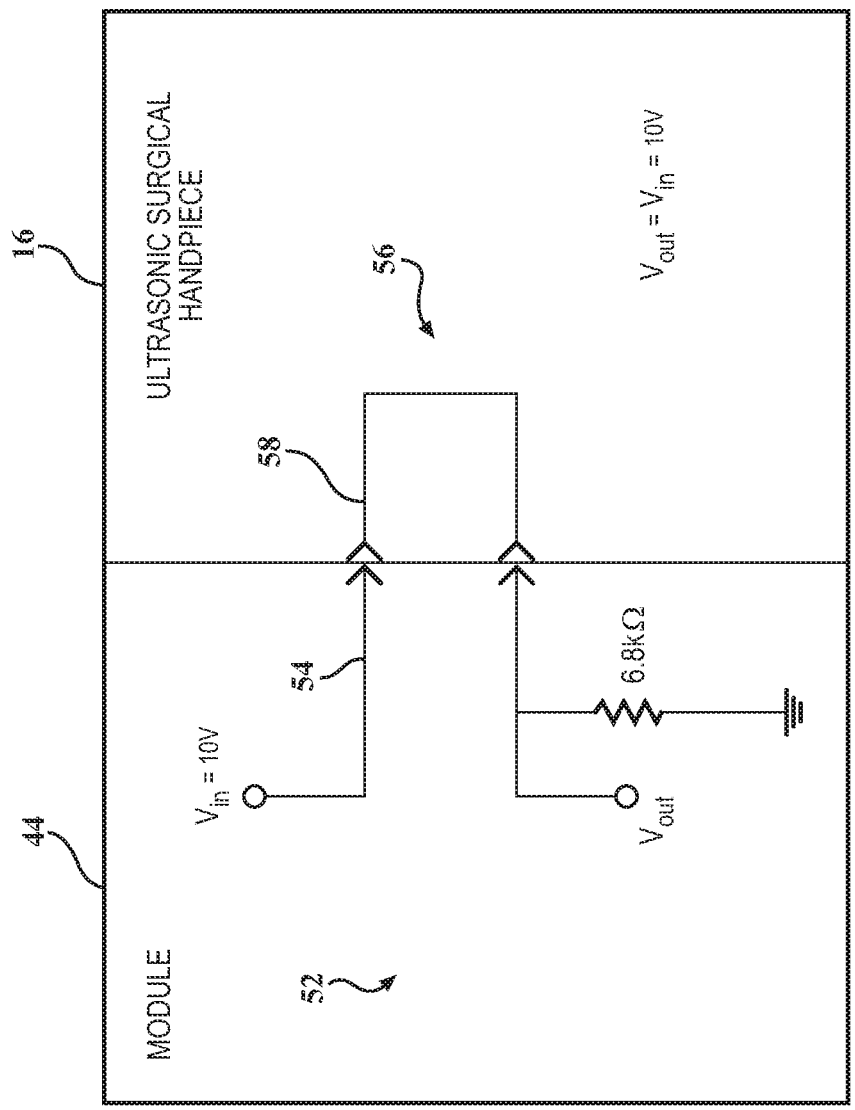
FIG. 2 is a schematic view of a module of the adapter and the ultrasonic surgical handpiece.

The module 44 is configured to detect the presence of the ultrasonic surgical handpiece 16 when the ultrasonic surgical handpiece 16 is coupled to the control console 14. In the instance shown in FIG. 2, the module 44 includes a circuit 52, which includes an input voltage $V_{in}$ of 10V and an output voltage $V_{out}$. The circuit 52 includes an open circuit 54 configured to receive an electrical component 56 of the ultrasonic surgical handpiece 16 when the ultrasonic surgical handpiece 16 is coupled to the adapter 10. In FIG. 2, the electrical component 56 of the ultrasonic surgical handpiece 16 is a short circuit 58. As shown, after the short circuit 58 of the ultrasonic surgical handpiece 16 is received by the open circuit 54 (e.g., when the connector 26 of the ultrasonic surgical handpiece 16 is coupled to the receptacle 24 of the adapter 10), the circuit 52 is completed and the output voltage $V_{out}$ switches from 0V to 10V. Accordingly, the module 44 transmits a handpiece presence signal 60 (shown in FIG. 1B) corresponding to the output voltage $V_{out}$ to a radio-frequency identification (RFID) device (shown as an RFID emulator 46 in FIG. 1B). In other instances, the electrical component 56 of the ultrasonic surgical handpiece 16 may include components other than a short circuit. For example, the electrical component of the surgical handpiece 16 may be: an active component, such as, but not limited to, a transistor, a diode, and/or a power source; a passive component, such as, but not limited to, a resistor, a capacitor, and/or an inductor; an electromechanical component, such as, but not limited to, a switch, a resettable fuse, a relay, and/or a connector; or combinations thereof. Additionally, the module 44 may transmit the handpiece presence signal 60 to the control console 14.

The adapter 10 also includes a radio-frequency identification (RFID) device, shown as the radio-frequency identification (RFID) emulator 46. The RFID emulator 46 is coupled to a memory 48 and to the connector 20. The memory 48 may include read-only memory (ROM), random access memory (RAM), flash memory, EEPROM, nonvolatile random access memory (NOVRAM), or any other suitable form of memory. In the instance shown in FIG. 1B, the adapter 10 includes the memory 48. However, in other instances, the memory 48 may be alternatively or additionally found in the surgical handpiece 16. One exemplary RFID emulator may be found in U.S. Pat. No. 10,061,948 B2, which is hereby incorporated by reference in its entirety.

In the instance of FIG. 1B, the memory 48 stores a maximum and minimum frequency 50 for driving the ultrasonic surgical handpiece 16. As such, the RFID emulator 46 is configured to transmit the maximum and minimum frequency 50 from the memory 48 to the control console 14 via the connector 20 using an RFID protocol. In instances where the adapter 10 includes the module 44, the RFID emulator 46 may transmit the maximum and minimum frequency 50 in response to the module 44 detecting the presence of the ultrasonic surgical handpiece 16. The control console 14 may then generate the drive signal 12 based on the maximum and/or minimum frequency 50 pertaining to the connected ultrasonic surgical handpiece 16 such that the adapter 10 may receive the drive signal 12 from the control console 14 and provide the drive signal 12 to the ultrasonic surgical handpiece 16.

The module 44 may also be configured to identify the ultrasonic surgical handpiece 16. In the instances shown in FIGS. 3A and 3B, the module 44 includes the circuit 52, which includes the input voltage $V_{in}$, the output voltage $V_{out}$, and the open circuit 54. Furthermore, in FIGS. 3A and 3B, the ultrasonic surgical handpieces 16 are a 25 kHz ultrasonic surgical handpiece 16' and a 34 kHz ultrasonic surgical handpiece 16", respectively, with "25 kHz" and "34 kHz" corresponding to a frequency of operation of the respective ultrasonic surgical handpieces 16', 16". Accordingly, the open circuit 54 is configured to receive the electrical component 56' of the ultrasonic surgical handpiece 16' and the electrical component 56" of the ultrasonic surgical handpiece 16". The module 44 then determines the identity of the ultrasonic surgical handpiece 16 as the 25 kHz ultrasonic surgical handpiece 16' or the 34 kHz ultrasonic surgical handpiece 16" based on the open circuit 54 receiving the electrical component 56' or 56". For example, in FIG. 3A, the 25 kHz ultrasonic surgical handpiece 16' includes a 1 kΩ resistor 62 as the electrical component 56'. Likewise, in FIG. 3B, the 34 kHz ultrasonic surgical handpiece 16" includes a 10 kΩ resistor 64 as the electrical component 56". As shown, after the electrical component 56' or 56" is received by the open circuit 54 (e.g., when the connector 26 of the ultrasonic surgical handpiece 16', 16" is coupled to the receptacle 24 of the adapter 10), the output voltage V out switches from 0V to 8.72V or 4.04V. Accordingly, the module 44 transmits a handpiece identification signal 66 (shown in FIG. 1B) corresponding to the output voltage V out to the RFID emulator 46. In other instances, the electrical components 56', 56" of the ultrasonic surgical handpieces 16', 16" may include other active, passive, or electromechanical components. Additionally, the module 44 may transmit the handpiece identification signal 66 to the control console 14.

As disclosed herein, it should be understood that, in instances where the module 44 is configured to identify the ultrasonic surgical handpiece 16, the module 44 determines the presence of the ultrasonic surgical handpiece 16 by identifying the ultrasonic surgical handpiece 16. In other words, by identifying the ultrasonic surgical handpiece 16, the module 44 is detecting the presence of the ultrasonic surgical handpiece 16. Therefore, in instances where a component of the ultrasonic surgical system 18 is configured to act "in response to detecting the presence of the ultrasonic surgical handpiece 16," the component of the ultrasonic surgical system 18 may also be configured to act in response to identifying the ultrasonic surgical handpiece 16.

In various instances, the module 44 may include any suitable combination of software and hardware components for detecting the presence of the ultrasonic surgical handpiece 16 or identifying the ultrasonic surgical handpiece 16. For example, in FIGS. 2, 3A, and 3B the module 44 includes a hardware component, the circuit 52, configured to receive the electrical components 56, 56', 56" of the ultrasonic surgical handpieces 16, 16', 16". The module 44 in FIGS. 2, 3A, and 3B also includes software components configured to determine the presence or the identity of the ultrasonic surgical handpieces 16, 16', 16" and to transmit the handpiece presence signal 60 or the handpiece identification signal 66 accordingly. In other instances, the module 44 may include a different combination of software and hardware components for detecting the presence of the ultrasonic surgical handpiece 16 or identifying the ultrasonic surgical handpiece 16.

Figure 4:
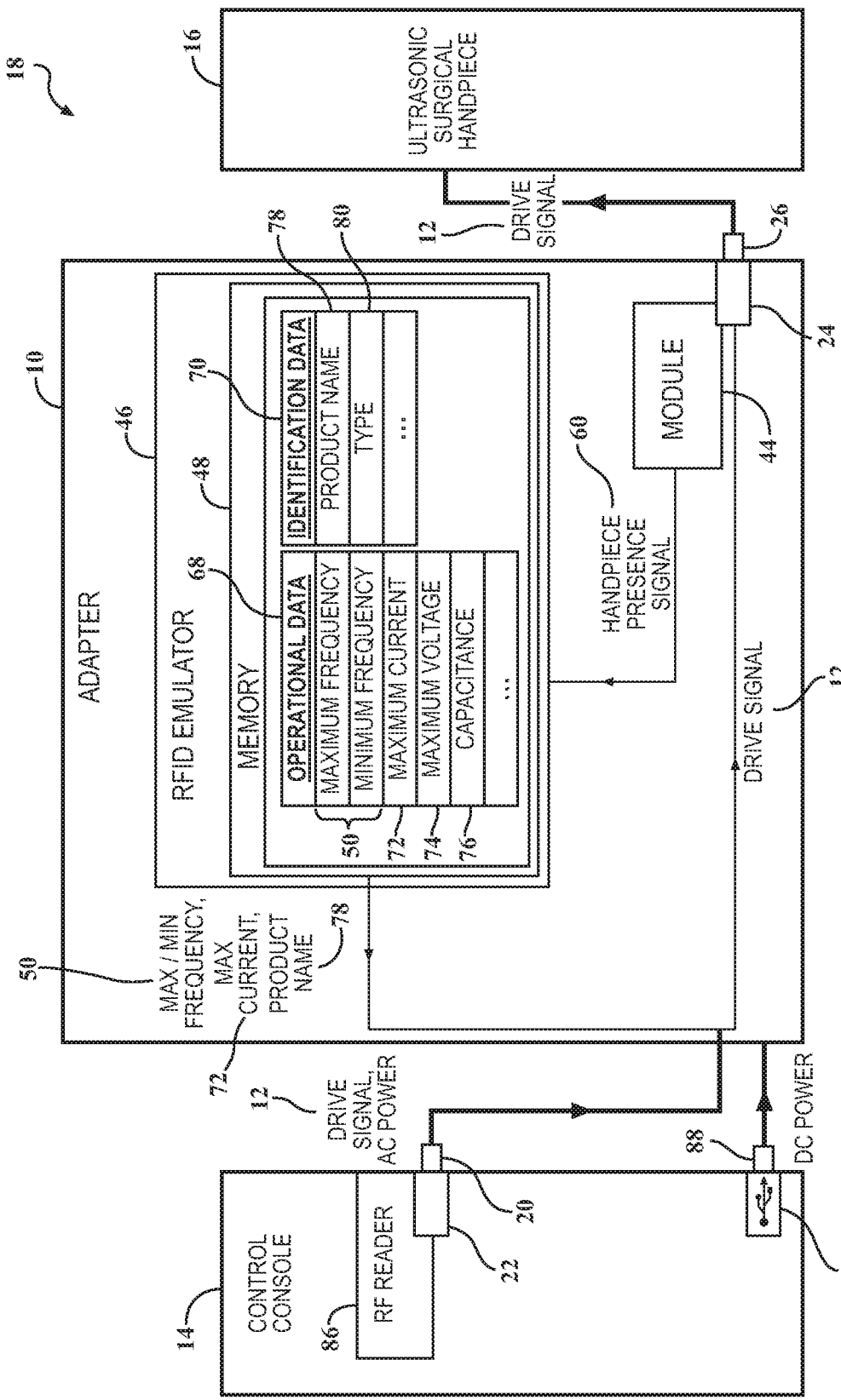
FIGS. 4 and 5 are schematic views of the ultrasonic surgical system, wherein a memory of the adapter is further illustrated.

Referring to FIG. 4, the RFID emulator 46 is configured to transmit the maximum and minimum frequency 50 from the memory 48 to the control console 14 via the connector 20 using an RFID protocol in response to the module 44 detecting the presence of the ultrasonic surgical handpiece 16. As shown, the RFID emulator 46 may be coupled to a memory 48, which includes data describing the characteristics of the ultrasonic surgical handpiece 16. For instance, in FIG. 4, the memory includes operational data 68 and identification data 70 of the ultrasonic surgical handpiece 16. The operational data 68 include a maximum and minimum frequency 50 of the drive signal 12, a maximum current 72 of the drive signal 12, a maximum voltage 74 of the drive signal 12, and/or a capacitance 76 of the ultrasonic surgical handpiece 16. The identification data includes a product name 78 of the ultrasonic surgical handpiece 16 (e.g., "Ultrasonic Surgical Handpiece for OR1") and/or a serial number (e.g. "8809-01"), and a type 80 of the ultrasonic surgical handpiece 16 (e.g., "25 kHz Ultrasonic Aspirator"). In FIG. 4, after receiving the handpiece presence signal 60, the RFID emulator 46 transmits the maximum and minimum frequency 50 and/or the maximum current 72 of the drive signal 12 from the memory 48 to the control console 14. However, in other instances, the RFID emulator 46 may transmit any data stored in the memory 48 to the control console 14. For example, as shown in FIG. 4, the RFID emulator 46 may also transmit the product name 78 of the ultrasonic surgical handpiece 16 from the memory 48 to the control console 14 for display on the display 28 (as shown in FIG. 1A). Additionally, the memory 48 may include any other suitable data, such as usage data of the surgical handpiece 16.

Figure 5:
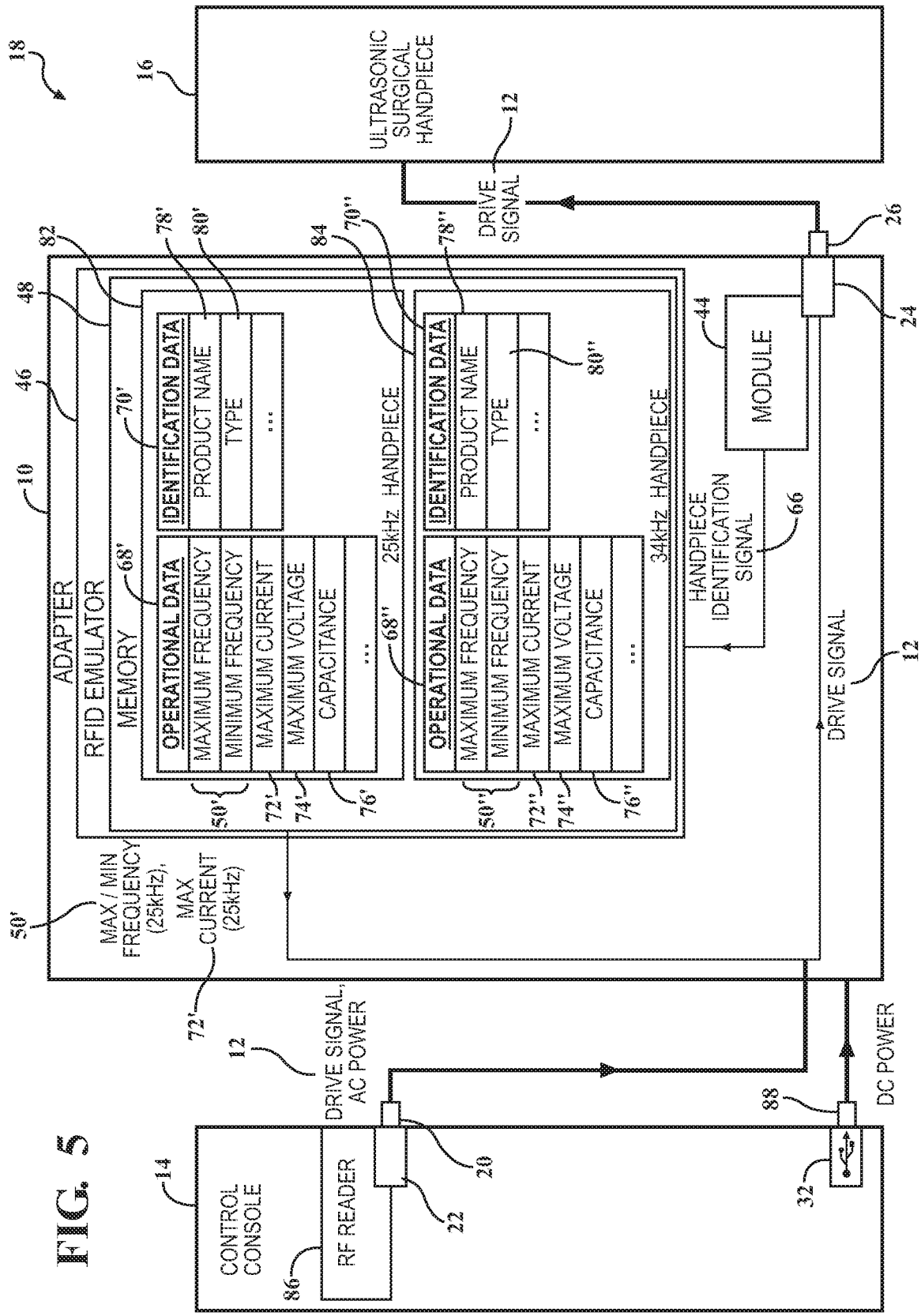

Referring to FIG. 5, the RFID emulator 46 is configured to transmit the maximum and minimum frequency 50 from the memory 48 to the control console 14 via the connector 20 using an RFID protocol in response to the module 44 identifying the presence of the ultrasonic surgical handpiece 16. In this instance, the memory 48 includes data corresponding to a variety of characteristics of the ultrasonic surgical handpiece 16. For example, in FIG. 5, the memory 48 includes data 82 corresponding to the characteristics of 25 kHz ultrasonic surgical handpiece 16' and data 84 corresponding to the characteristics of 34 kHz ultrasonic surgical handpiece 16". Each of the data 82 and 84 includes operational data 68', 68" and identification data 70', 70" of the respective handpieces 16', 16". The operational data 68', 68" include a maximum and minimum frequency 50', 50" of the drive signal 12, a maximum current 72', 72" of the drive signal 12, a maximum voltage 74', 74" of the drive signal 12, and a capacitance 76', 76" of the ultrasonic surgical handpiece 16. The identification data 70', 70" include a product name 78', 78" of the ultrasonic surgical handpiece 16 (e.g., "Ultrasonic Surgical Handpiece for OR1") and/or a serial number (e.g. "8809-01"), and a type 80', 80" of the ultrasonic surgical handpiece 16 (e.g., "25 kHz Ultrasonic Aspirator"). In FIG. 5, the module 44 identifies the ultrasonic surgical handpiece 16 as the 25 kHz ultrasonic surgical handpiece 16'. As such, the module 44 transmits the handpiece identification signal 66 and the RFID emulator 46 transmits the maximum and minimum frequency 50' and the maximum current 72' of the drive signal 12 for the 25 kHz ultrasonic surgical handpiece 16' from the memory 48 to the control console 14. In other instances, the RFID emulator 46 may transmit any data stored in the memory 48 to the control console 14 based on the handpiece identification signal 66. Additionally, the memory 48 may include any other suitable data for the ultrasonic surgical handpieces 16', 16". Furthermore, the memory may also include data for a variety of other suitable ultrasonic surgical handpieces 16.

The RFID emulator 46 is referred to as an "RFID emulator" because the RFID emulator 46 transmits data from the memory 48 to the control console 14 via the connector 20 using an RFID protocol. For example, the RFID protocol may specify a number of bits for an RFID data transmission and an encryption format for the RFID data transmitted to the control console 14. In FIG. 1B, the RFID emulator 46 transmits the maximum and minimum frequency 50 from the memory 48 to the control console 14 via the connector 20.

In other instances, the RFID device may include a device other than the RFID emulator 46. For example, the RFID device may be any device suitable for transmitting data from the memory 48 to the control console 14 via the connector 20 using an RFID protocol. In one such example, the RFID device may include a radio-frequency (RF) reader (not shown) and an RFID tag (not shown) including the memory 48. In such an example, the RF reader receives a wireless RF signal from the RFID tag, the wireless RF signal including data from the memory 48. The RF reader then transmits the data from the memory 48 to the control console 14 via the connector 20 using an RFID protocol.

The adapter 10 may include a controller (not shown) configured to relay communication between the module, the RFID device, the receptacle 24, and/or the control console. For example, the module 44 and the RFID emulator 46 may be coupled to the controller such that the module 44 may transmit the handpiece presence signal 60 or the handpiece identification signal 66 to the RFID emulator 46 via the controller. Similarly, the control console 14 may be coupled to the controller such that the RFID emulator 46 transmits the maximum and minimum frequency 50 to the control console 14 via the controller. Likewise, the receptacle 24 may be coupled to the controller such that the control console 14 transmits the drive signal 12 to the receptacle 24 and ultimately to the ultrasonic surgical handpiece 16 via the controller.

The adapter 10 may receive AC power from the control console 14 via the connector 20. As shown in FIG. 1B, the control console 14 may include a radio-frequency (RF) reader 86. The RF reader 86 may be configured to transmit electromagnetic signals to interrogate nearby passive RF devices. The control console 14 may be configured to provide the electromagnetic signals to the adapter 10 in the form of AC power via the connector 20 upon the connector 20 being coupled to the receptacle 22. In such instances, the adapter 10 may receive the AC power from the RF reader 86, which may then be received by the module 44 and the memory 48 of the adapter 10.

The adapter 10 may also receive direct current (DC) power from the control console 14 or from a battery. As previously described and as shown in FIGS. 1B and 6, the control console 14 may include the USB port 32 configured to receive a USB connector 88. Additionally, the adapter 10 may include a USB connector 88, shown in FIGS. 1B and 6, such that the adapter 10 receives DC power from the control console 14 upon the USB connector 88 being coupled to the USB port 32. In such instances, the module 44 and the memory 48 of the adapter 10 may then receive the DC power.

Figure 7A:
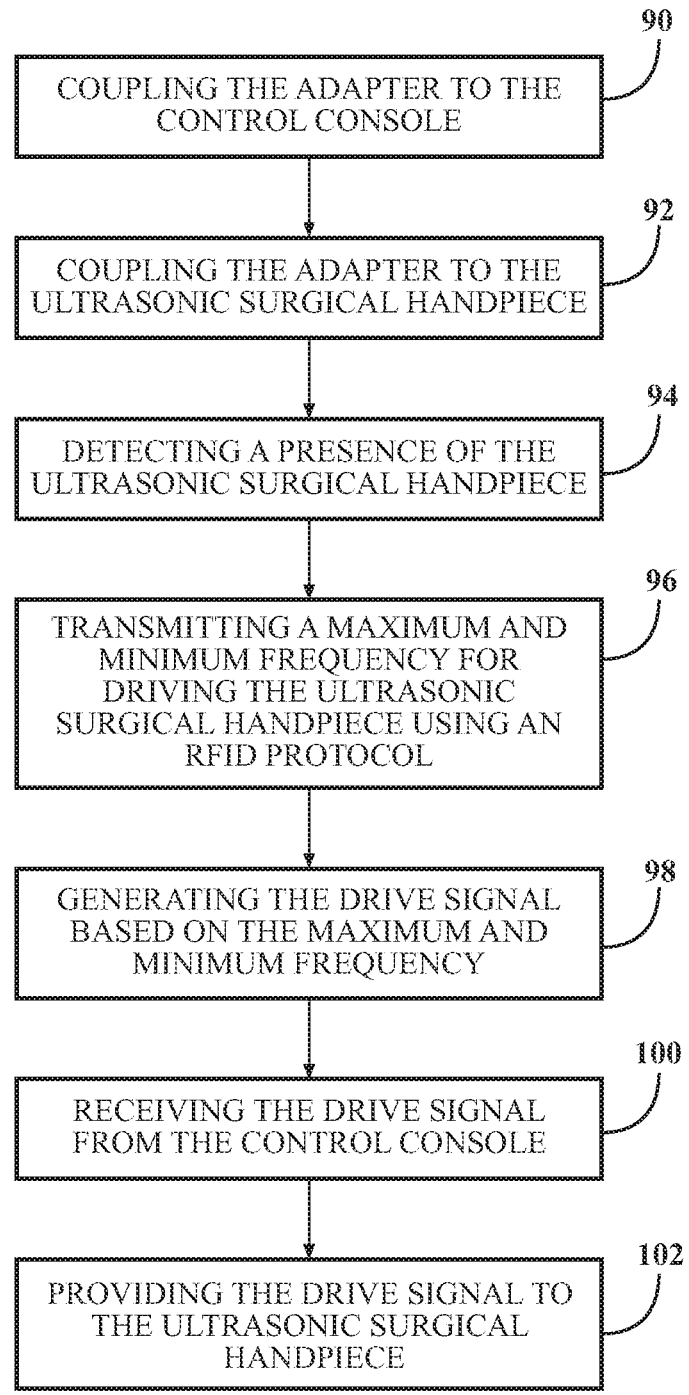
FIG. 7A is a block diagram of a method of operating the ultrasonic surgical system.

Referring to FIG. 7A, a method of operating the ultrasonic surgical system 18 of FIG. 1A is shown. The method includes a step 90 of coupling the adapter 10 to the control console 14 via the connector 20; a step 92 of coupling the adapter 10 to the ultrasonic surgical handpiece 16; a step 94 of detecting, by the module 44 of the adapter 10, the presence of the ultrasonic surgical handpiece 16; a step 96 of transmitting, by the RFID emulator 46 of the adapter 10, a maximum and minimum frequency 50 for driving the ultrasonic surgical handpiece 16 to the control console 14 via the connector 20 using an RFID protocol in response to the module 44 detecting the presence of the ultrasonic surgical handpiece 16; a step 98 of generating, by the control console 14, the drive signal 12 based on the maximum and minimum frequency 50 for driving the ultrasonic surgical handpiece 16; a step 100 of receiving, by the adapter 10, the drive signal 12 from the control console 14 via the connector 20; and a step 102 of providing, by the adapter 10, the drive signal 12 to the ultrasonic surgical handpiece 16. The steps 90, 92, 94, 96, 98, 100, and 102 are further shown in FIG. 1B.

Steps of the method described herein may be ordered in any suitable order to operate the ultrasonic surgical system 18 to provide the drive signal 12 to the ultrasonic surgical handpiece 16. For example, in some instances, the step 92 of coupling the adapter 10 to the ultrasonic surgical handpiece 16 may occur before the step 90 of coupling the adapter 10 to the control console 14.

Figure 7B:
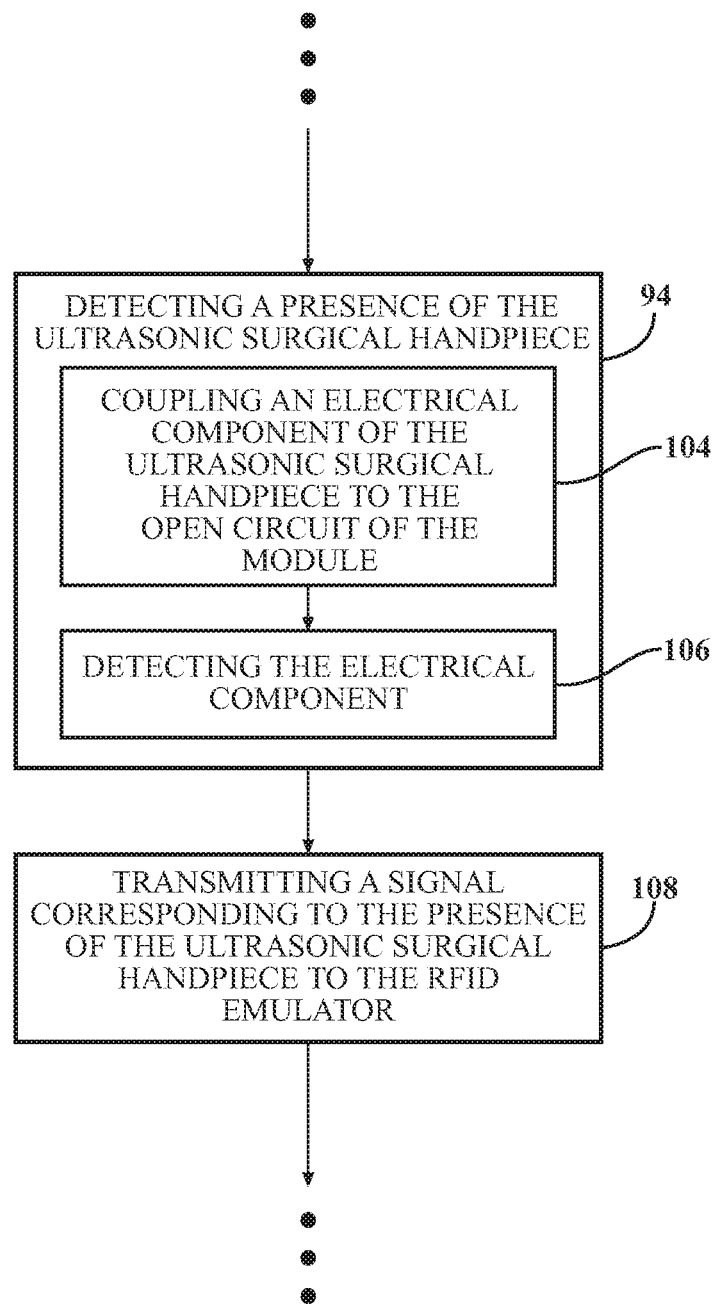
FIG. 7B is a block diagram of steps of detecting a presence of the ultrasonic surgical handpiece.

The step 94 of detecting the presence of the ultrasonic surgical handpiece 16 is further shown in FIG. 7B. As previously described, the module 44 may include the open circuit 54 (shown in FIG. 2), and the ultrasonic surgical handpiece 16 may include the electrical component 56 (also shown in FIG. 2). In such instances, the step 94 includes a step 104 of coupling the electrical component 56 to the open circuit 54. Additionally, the step 94 includes a step 106 of detecting the presence of the electrical component 56 of the ultrasonic surgical handpiece 16. The steps 94, 104, and 106 are shown in FIG. 2, wherein the electrical component 56 is coupled to the open circuit 54 and the output voltage $V_{out}$ switches from 0V to 10V.

In FIG. 7B, the method further includes a step 108 of transmitting, by the module 44, the handpiece presence signal 60 (shown in FIG. 4) to the RFID emulator 46. In some instances, during step 108, the module 44 may transmit the handpiece presence signal 60 to the control console 14.

Figure 3B:
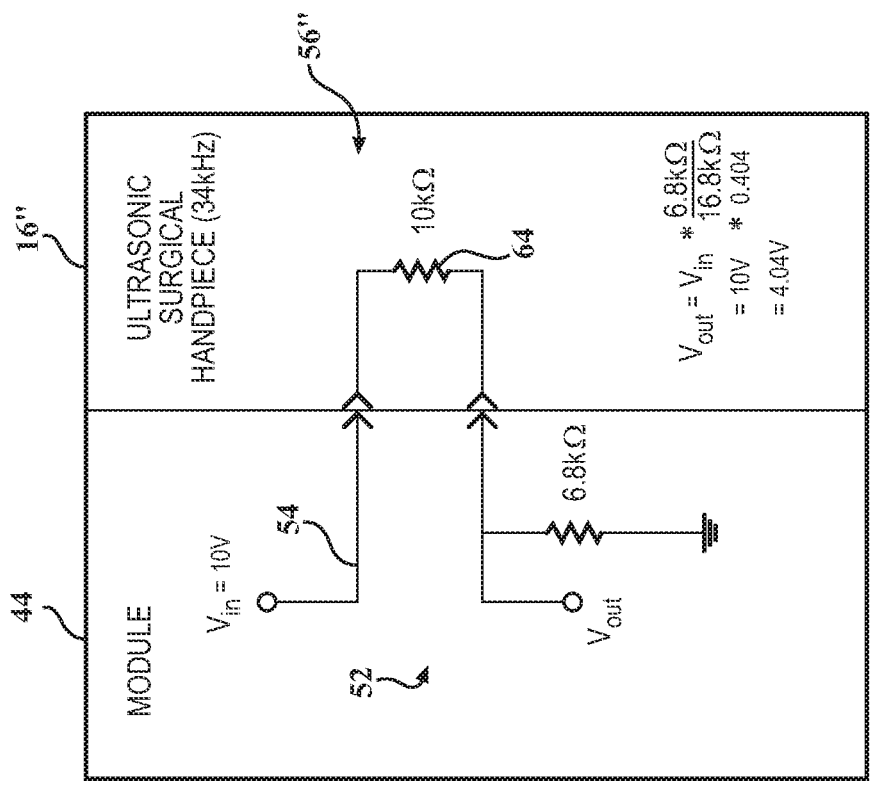
FIG. 3B is a schematic view of the module of the adapter and a second type of ultrasonic surgical handpiece.
Figure 3A:
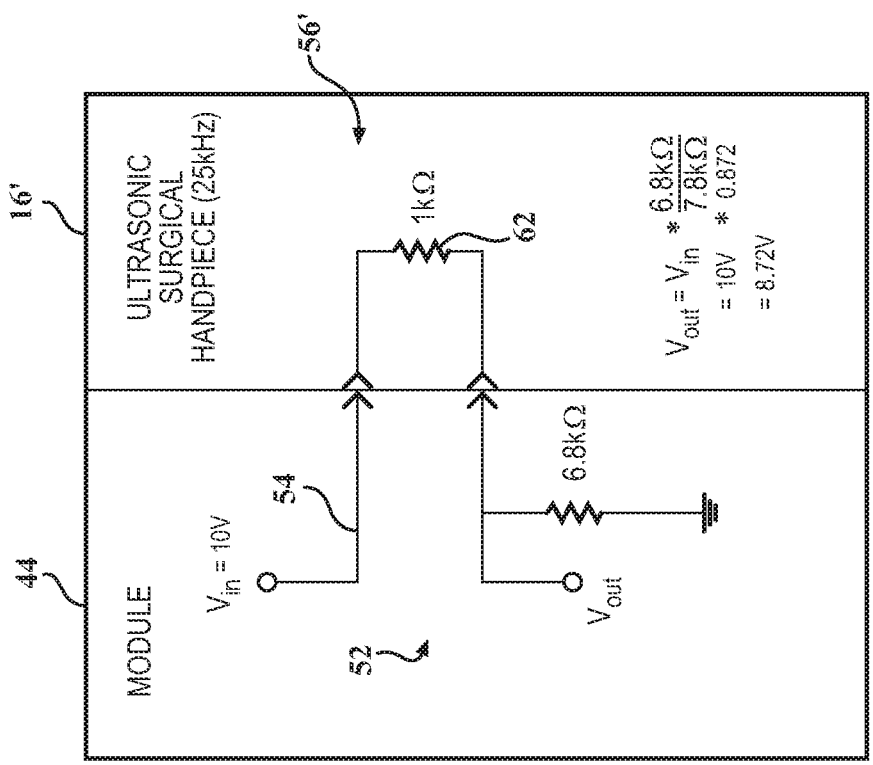
FIG. 3A is a schematic view of the module of the adapter and a first type of ultrasonic surgical handpiece.
Figure 7C:
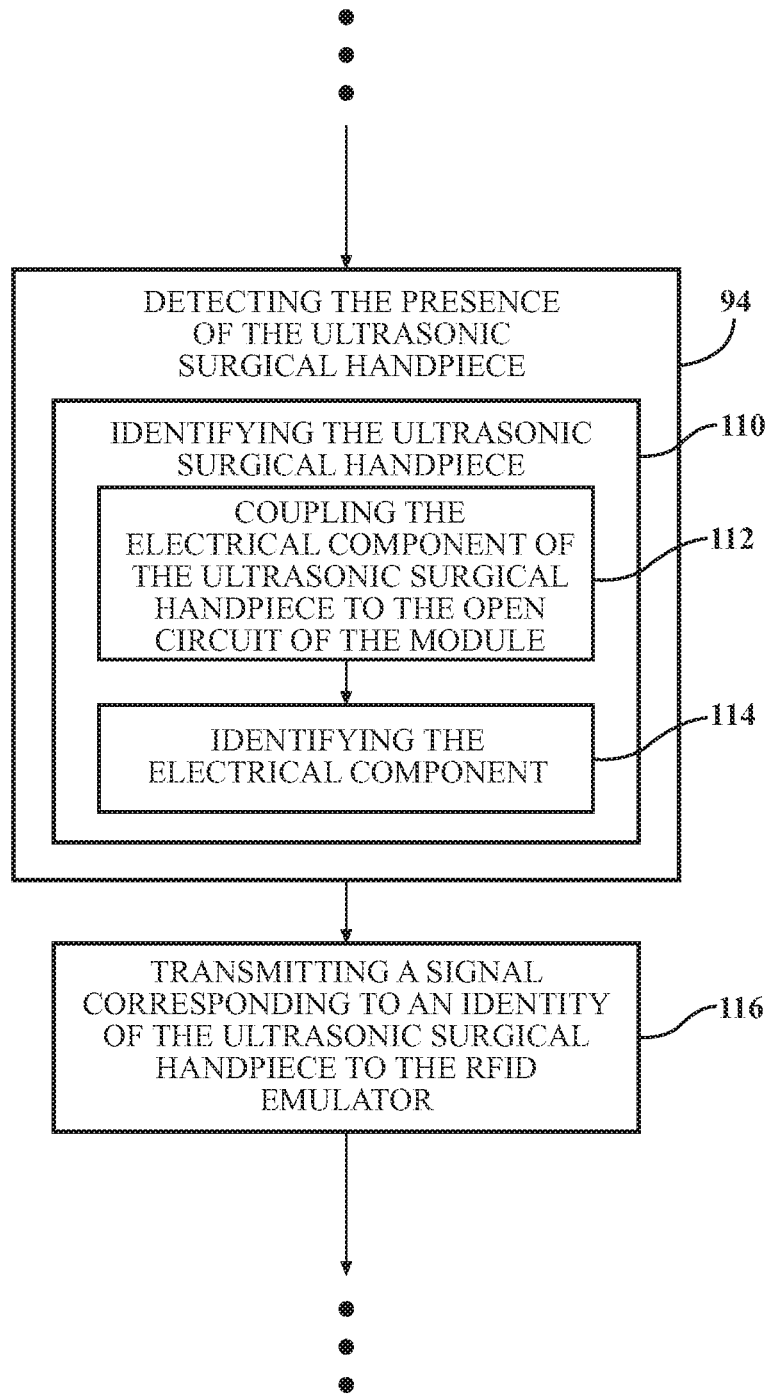
FIG. 7C is a block diagram of steps of identifying an ultrasonic surgical handpiece.

FIG. 7C illustrates an instance where the step 94 of detecting the presence of the ultrasonic surgical handpiece 16 includes a step 110 of identifying, by the module 44, the ultrasonic surgical handpiece 16. In such instances, the module 44 may include the open circuit 54 (shown in FIGS. 3A and 3B). Furthermore, in such instances, the ultrasonic surgical handpiece 16 may include an electrical component. For example, in the instance of FIGS. 3A and 3B, wherein the module 44 is configured to identify the 25 kHz ultrasonic surgical handpiece 16' and/or the 34 kHz ultrasonic surgical handpiece 16", the 25 kHz and 34 kHz ultrasonic surgical handpieces 16', 16" include a 1 kΩ resistor 62 and a 10 kΩ resistor 64 as the electrical components 56', 56", respectively. In FIG. 7C, the step 110 includes a step 112 of coupling the electrical component 56' or 56" to the open circuit 54 of the module 44 and a step 114 of identifying the electrical component 56' or 56". The steps 110, 112, and 114 are shown in FIGS. 3A and 3B, wherein the electrical component 56' or 56" is coupled to the open circuit 54 and the output voltage $V_{out}$ switches from 0V to either 8.72V or 4.04V, based on the electrical component 56' or 56" coupled to the open circuit 54, and consequently, the ultrasonic surgical handpiece 16' or 16" coupled to the adapter 10.

In FIG. 7C, the method further includes a step 116 of transmitting, by the module 44, the handpiece identification signal 66 (shown in FIG. 5) to the RFID emulator 46. In some instances, during step 116, the module 44 may transmit the handpiece identification signal 66 to the control console 14.

Figure 7D:
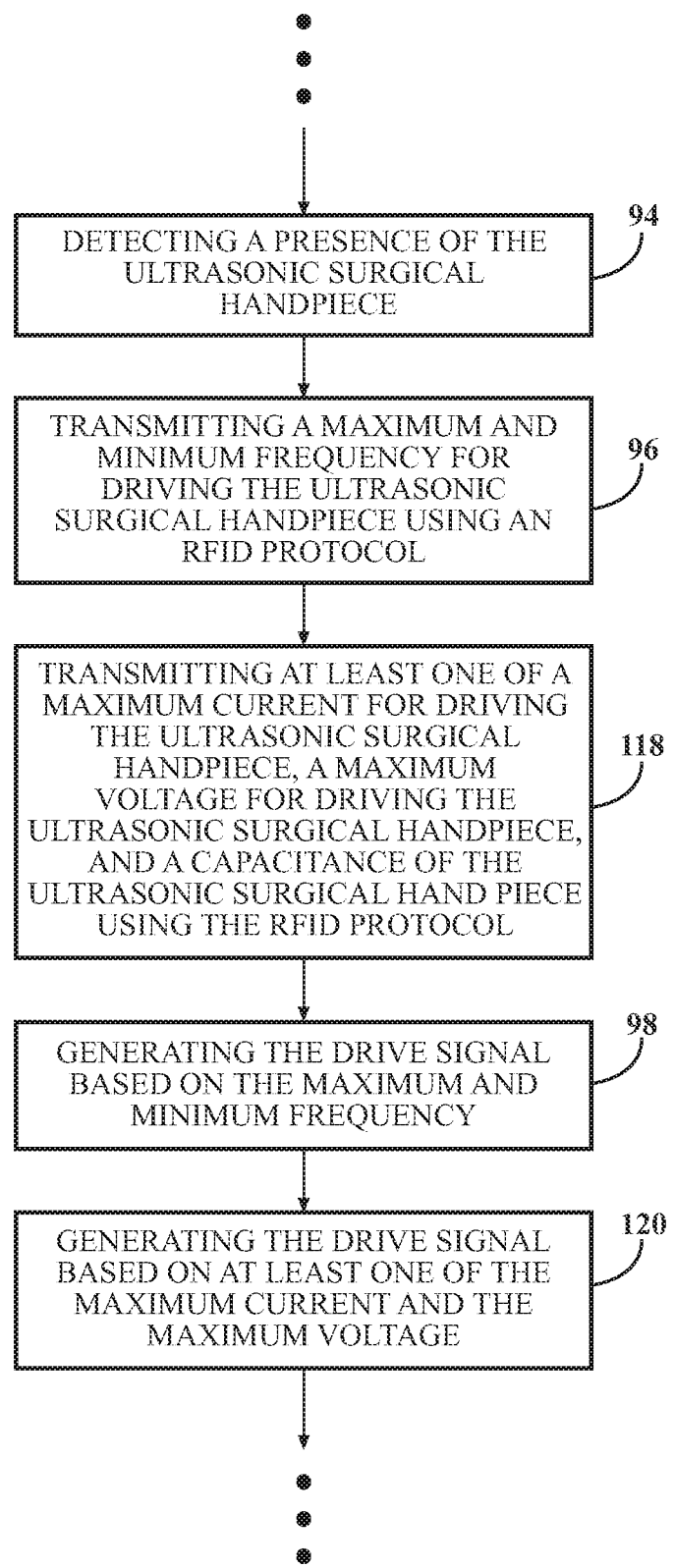
FIG. 7D is a block diagram of steps of transmitting operational data of the ultrasonic surgical handpiece to the control console.

In the instance of FIG. 7D, the method further includes a step 118 of transmitting, by the RFID emulator 46, at least one of a maximum current 72 for driving the ultrasonic surgical handpiece 16, a maximum voltage 74 for driving the ultrasonic surgical handpiece 16, and a capacitance 76 of the ultrasonic surgical handpiece 16 via the connector 20 using the RFID protocol in response to the module 44 detecting the presence of the ultrasonic surgical handpiece 16 during step 94. The method also includes a step 120 of generating the drive signal 12 based on at least one of the maximum current 72 for driving the ultrasonic surgical handpiece 16, the maximum voltage 74 for driving the ultrasonic surgical handpiece 16, and the capacitance 76 of the ultrasonic surgical handpiece 16. Steps 94, 96, 118, and 120 are further illustrated in FIG. 4, wherein the RFID emulator 46 transmits the maximum current 72 and the maximum and minimum frequency 50 from the memory 48 to the control console 14 in response to receiving the handpiece presence signal 60, and the control console 14 generates the drive signal 12 based on the maximum current 72 and the maximum and minimum frequency 50.

Figure 7E:
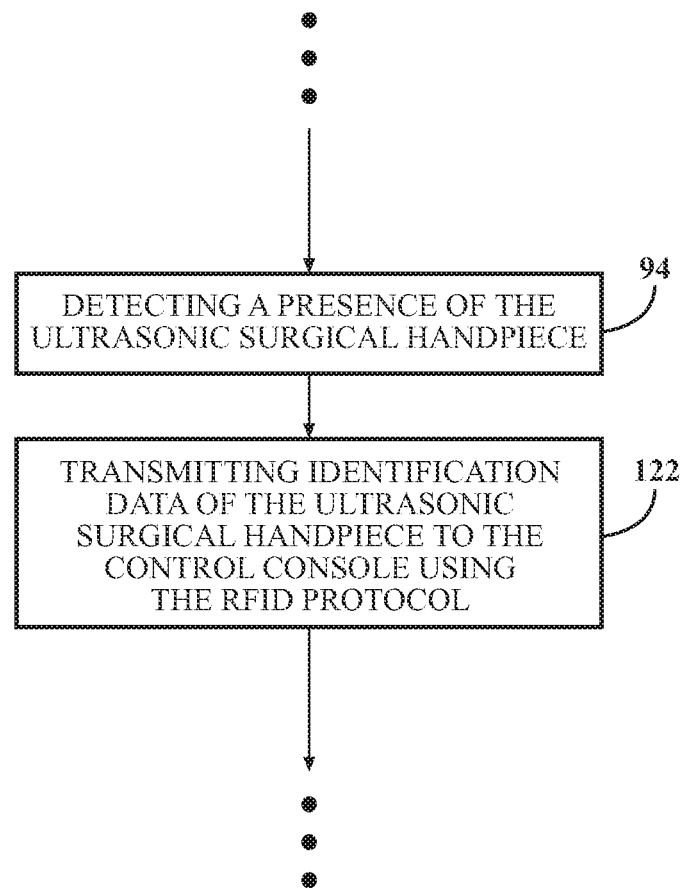
FIG. 7E is a block diagram of steps of transmitting identification data of the ultrasonic surgical handpiece to the control console.

FIG. 7E illustrates an instance where the method further includes a step 122 of transmitting, by the RFID emulator 46 of the adapter 10, identification data 70 of the ultrasonic surgical handpiece 16 from the memory 48 to the control console 14 via the connector 20 using the RFID protocol in response to the module 44 detecting the presence of the ultrasonic surgical handpiece 16 during step 94. Steps 94 and 122 are further illustrated in FIG. 4, wherein the RFID emulator 46 transmits the product name 78 from the memory 48 to the control console 14 in response to receiving the handpiece presence signal 60.

Figure 7F:
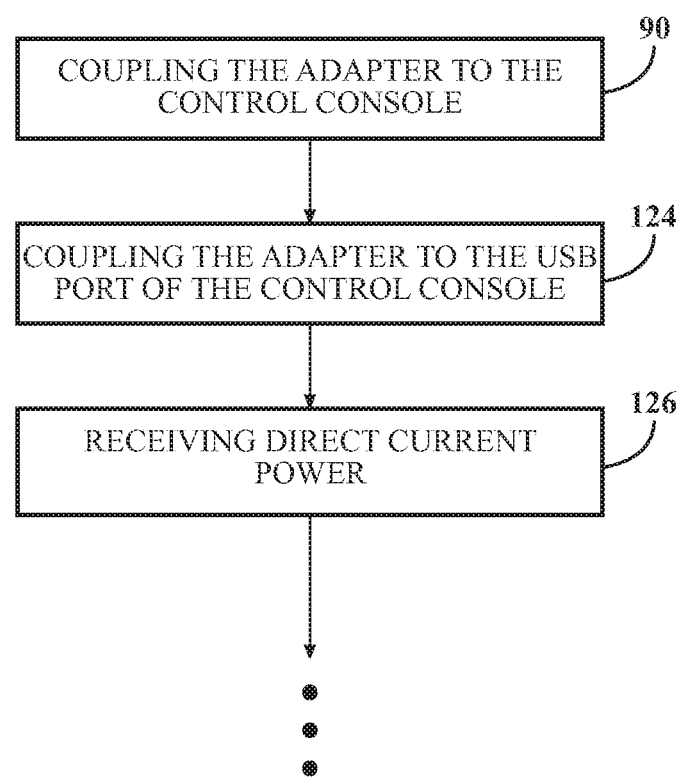
FIG. 7F is a block diagram of steps of receiving direct current (DC) power by the adapter.

As previously stated, the adapter 10 may be configured to receive DC power. In FIG. 7F, an instance where the method includes a step 126 of receiving DC power by the adapter 10 is shown. As shown, prior to step 126, the method includes a step 124, wherein the adapter 10 is coupled to the USB port 32 of the control console 14. Step 124 is illustrated in FIG. 6, wherein the USB connector 88 of the adapter 10 is coupled to the USB port 32. Thus, the adapter 10 receives DC power from the control console 14.

Figure 7G:
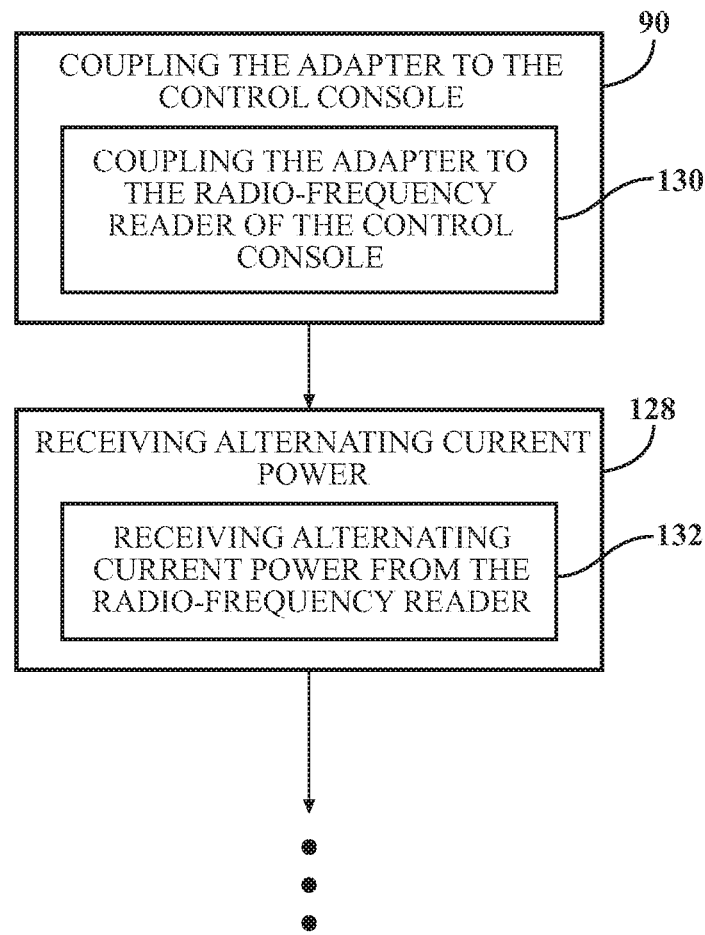
FIG. 7G is a block diagram of steps of receiving alternating current (AC) power by the adapter.

As also previously stated, the adapter 10 may be configured to receive AC power. In FIG. 7G, an instance where the method includes a step 128 of receiving AC power by the adapter 10 is shown. In such an instance, the step 92 of coupling the adapter 10 to the control console 14 includes a step 130 of coupling the adapter 10 to the RF reader 86 of the control console 14. As shown in FIG. 1B, the adapter 10 may be coupled to the RF reader 86 of the control console 14 by coupling the connector 20 to the receptacle 22 of the control console 14. As such, during a step 132, the adapter 10 receives AC power from the RF reader 86 of the control console 14. Step 132 is also further shown in FIG. 1B, wherein the RF reader 86 transmits AC power to the adapter 10 via the connector 20.

It will be further appreciated that the terms "include," "includes," and "including" have the same meaning as the terms "comprise," "comprises," and "comprising."

Several examples have been discussed in the foregoing description. However, the examples discussed herein are not intended to be exhaustive or limit the disclosure to any particular form. The terminology which has been used is intended to be in the nature of words of description rather than of limitation. Many modifications and variations are possible in light of the above teachings and the disclosure may be practiced otherwise than as specifically described.

What is claimed is:

1. An adapter configured to receive a drive signal from a control console and to provide the drive signal to a surgical handpiece to operate the surgical handpiece, the adapter comprising:
   a receptacle configured to receive a connector of the surgical handpiece and provide the drive signal to the surgical handpiece to operate the surgical handpiece;
   a connector configured to be inserted into a receptacle of the control console, wherein the connector of the adapter is configured to receive the drive signal from the control console when the connector of the adapter is coupled to the control console; and
   a radio-frequency identification device coupled to the connector of the adapter, wherein the radio-frequency identification device is coupled to a memory storing data indicating a drive signal characteristic for the surgical handpiece, the radio-frequency identification device being configured to transmit the drive signal characteristic data from the memory to the control console through the connector of the adapter using an RFID protocol.

2. The adapter of claim 1, wherein the adapter comprises a module configured to detect a presence of the surgical handpiece, and wherein the radio-frequency identification device is configured to transmit the drive signal characteristic data from the memory to the control console in response to the module detecting the presence of the surgical handpiece.

3. The adapter of claim 2, wherein the module comprises an open circuit, the open circuit being configured to receive an electrical component of the surgical handpiece.

4. The adapter of claim 3, wherein the module is further configured to determine a presence of the surgical handpiece based on the open circuit receiving the electrical component and to transmit a signal corresponding to the presence of the surgical handpiece to the radio-frequency identification device.

5. The adapter of claim 2, wherein the module is further configured to identify the surgical handpiece.

6. The adapter of claim 5, wherein the module comprises an open circuit, the open circuit being configured to receive an electrical component of the surgical handpiece.

7. The adapter of claim 6, wherein:
   the module is further configured to determine an identity of the surgical handpiece based on the open circuit receiving the electrical component and to transmit a signal corresponding to the identity of the surgical handpiece to the radio-frequency identification device; and
   the radio-frequency identification device is further configured to transmit the drive signal characteristic data from the memory to the control console via the connector of the adapter using the RFID protocol in response to the module identifying the surgical handpiece.

8. The adapter of claim 2, wherein the connector of the adapter is further defined as a first connector, and wherein the adapter is configured to be coupled to a USB port of the control console via a second connector of the adapter, the module and the memory of the adapter being configured to receive direct current power from the USB port of the control console via the second connector.

9. The adapter of claim 2, wherein the adapter is configured to be coupled to a radio-frequency reader of the control console via the connector of the adapter, the module and the memory of the adapter being configured to receive alternating current power from the radio-frequency reader via the connector of the adapter.

10. The adapter of claim 1, wherein the adapter is configured to receive direct current power.

11. The adapter of claim 1, wherein the adapter is configured to power the radio-frequency identification device with alternating current power received from the control console.

12. The adapter of claim 1, wherein the memory further stores identification data.

13. The adapter of claim 12, wherein the identification data comprises at least one of a product name and a type of the surgical handpiece.

14. The adapter of claim 1, wherein the radio-frequency identification device is an RFID emulator.

15. A method of operating a system for providing a drive signal to a surgical handpiece to operate the surgical handpiece, the system comprising the surgical handpiece, a control console, and an adapter, the method comprising steps of:
   inserting a connector of the adapter into a receptacle of the control console, the connector being configured to receive the drive signal from the control console when the connector is coupled to the control console;
   receiving in a receptacle of the adapter a connector of the surgical handpiece, the receptacle configured to provide the drive signal to the surgical handpiece to operate the surgical handpiece;
   transmitting, by a radio-frequency identification device of the adapter that is coupled to the connector of the adapter and a memory, data stored in the memory that indicates a drive signal characteristic for the surgical handpiece from the memory to the control console through the connector of the adapter using an RFID protocol;
   receiving, by the adapter, the drive signal from the control console via the connector of the adapter; and
   providing, by the adapter, the drive signal to the surgical handpiece to operate the surgical handpiece.

16. The method of claim 15, further comprising a step of generating, by the control console, the drive signal based on the drive signal characteristic data for driving the surgical handpiece.

17. The method of claim 15, wherein the adapter comprises an open circuit, and further comprising steps of coupling an electrical component of the surgical handpiece to the open circuit, detecting, by the adapter, a presence of the surgical handpiece based on the open circuit receiving the electrical component of the surgical handpiece, and transmitting, by the radio-frequency identification device, the drive signal characteristic data from the memory to the control console in response to the adapter detecting the presence of the surgical handpiece.

18. The method of claim 15, wherein the adapter comprises an open circuit, and further comprising steps of:
- coupling an electrical component of the surgical handpiece to the open circuit;
- determining, by the adapter, an identity of the surgical handpiece based on the open circuit receiving the electrical component of the surgical handpiece; and
- transmitting a signal corresponding to the identity of the surgical handpiece to the radio-frequency identification device.

* * * * *